US007435805B2

(12) United States Patent  
Kidemet et al.

(10) Patent No.: US 7,435,805 B2
(45) Date of Patent: Oct. 14, 2008

(54) O-ALKYL MACROLIDE AND AZALIDE DERIVATIVES AND REGIOSELECTIVE PROCESS FOR THEIR PREPARATION

(75) Inventors: Davor Kidemet, Varazdin (HR); Gorjana Lazarevski, Zagreb (HR); Marko Derek, Zagreb (HR); Marija Leljak, Durmanec (HR)

(73) Assignee: GlaxpSmithkline Istrazivacki, Zagreb (HR)

( * ) Notice: Subject to any disclaimer, the term of this patent is extended or adjusted under 35 U.S.C. 154(b) by 247 days.

(21) Appl. No.: 10/851,768

(22) Filed: May 21, 2004

(65) Prior Publication Data
US 2005/0164958 A1    Jul. 28, 2005

Related U.S. Application Data

(60) Provisional application No. 60/474,348, filed on May 30, 2003, provisional application No. 60/499,817, filed on Sep. 2, 2003.

(51) Int. Cl.
*C07H 17/08* (2006.01)
(52) U.S. Cl. .................... 536/7.4; 536/7.2; 536/18.6
(58) Field of Classification Search ................ 536/7.2, 536/7.4, 18.6; 514/29
See application file for complete search history.

(56) References Cited

U.S. PATENT DOCUMENTS 6,420,537 B1 * 7/2002 Bosch et al. ................. 536/7.4
6,593,360 B1 * 7/2003 Lazarevski et al. .......... 514/460

FOREIGN PATENT DOCUMENTS

EP    0 080 819 A1    6/1983
EP    0 467 331 A1    1/1992
WO    WO-99/20639 A2    4/1999

OTHER PUBLICATIONS

Evtushenko, Evgeny V., "Regioselective methylation of methyl glycopyranosides with diazomethane in the presence of transition-metal chlorides and of boric acid", Carbohydrate Research, vol. 316, pp. 187-200 (1999).
Bertho, Gildas, et al., "Solution confirmation of methylated macrolide antibiotics roxithromycin and erythromycin using NMR and molecular modelling. Ribosome-bound conformation determined by TRNOE and formation of cytochrome P450-metabolite complex", International Journal of Biological Macromolecules, vol. 22, pp. 103-127 (1998).
Waddell, Sherman T., et al., "Synthesis and antibacterial activity of O-methyl derivatives of azalide antibiotics: I. 4", 11 and 12-OMe derivatives via direct methylation", Bioorganic & Medicinal Chemistry Letters, vol. 8, No. 5, Mar. 3, 1998, pp. 549-554.
Morimoto Shigeo, et al., "Chemical modifications of erythromycins. II. Synthesis and antibacterial activity of o-alkyl derivatives of erythromycin A", Journal of Antibiotics, Japan Antibiotics Research Association, vol. 43, pp. 286-294 (1990.).

* cited by examiner

*Primary Examiner*—Elli Peselev
(74) *Attorney, Agent, or Firm*—Karen L. Prus

(57) ABSTRACT

The present disclosure relates to new 11-O-alkyl macrolides and azalides and pharmaceutically acceptable salts and solvates thereof, and to pharmaceutical compositions thereof. The disclosure also relates to a process for the preparation of 11-O-alkyl macrolides and azalides by regioselective 11-O-alkylation of macrolides and azalides having a vicinal diol system, using diazoalkanes in the presence of transition-metal halides or boric acid as catalysts. In another aspect, the disclosure relates to uses of the 11-O-alkyl macrolides and azalides as antibacterial agents or intermediates for the synthesis of other antibacterial agents.

2 Claims, No Drawings

O-ALKYL MACROLIDE AND AZALIDE DERIVATIVES AND REGIOSELECTIVE PROCESS FOR THEIR PREPARATION

Under 35 U.S.C. § 119(e), this application claims the benefit of prior U.S Provisional Application No. 60/474,348, filed May 30, 2003, and prior U.S. Provisional Application No. 60/499,817, filed Sep. 2, 2003, which are incorporated herein by reference in their entirety.

TECHNICAL FIELD

In one aspect, the present invention relates to a process for regioselective O-alkylation of macrolides and azalides applicable on a large scale. Specifically, the invention relates to regioselective 11-O-alkylation of macrolides and azalides having vicinal diol system, using diazoalkanes in the presence of transition-metal halides or boric acid as catalysts. In another aspect, the invention relates to 11-O-alkyl macrolides and azalides obtained according to the above mentioned process, pharmaceutically acceptable salts and solvates thereof and uses thereof as antibacterial agents or intermediates for the synthesis of other antibacterial agents.

BACKGROUND OF THE INVENTION

Several O-alkyl derivatives of macrolide and azalide antibiotics have been described in the literature. Among them O-methyl derivatives of erythromycin (clarithromycin) (U.S. Pat. No. 4,331,803) and azithromycin (U.S. Pat. No. 5,250,518) have significant biological activity. The process for preparing O-alkyl derivatives of macrolides and azalides is typically a multistep procedure. Because macrolide and azalide compounds posses several hydroxyl groups it has previously been difficult to alkylate one hydroxyl group selectively in the presence of other unprotected hydroxyl or amino groups (see e.g. J. Antibiot. 46 (1993) 647, 1239; J. Antibiot. 43 (1990) 286). In order to carry out selective O-alkylation of macrolides and azalides, the use of various protecting groups has been described in the literature (see e.g. J. Antibiot. 45 (1992) 527, J. Antibiot. 37 (1984) 187, J. Antibiot. 46 (1993) 1163, U.S. Pat. Nos. 5,872,229; 5,719,272and 5,929,219). Specifically, the multistep selective synthesis of 12-O-methyl azithromycin has been described in WO 99/20639. However, the selective substitution at the 11-O-position with alkyl group is not easily accomplished by prior art methods and is accompanied by side reactions, by-products and low yields.

Generally, the classical method for O-methylation of macrolides and azalides proceedes by initial protection of the reactive sites on the desosamine, typically as 2'-OCbz-3'NMeCbz. Such protected derivative is then O-methylated in a dipolar aprotic solvent (e.g. DMSO/THF or DMF) using a base (e.g. KOH or NaH) and methyl iodide. Removal of the Cbz's and Eschwiler-Clarke methylation of the 3'-nitrogen completes the sequence. It should be noted that there are four hydroxyls that can be methylated (4", 6, 11 and 12) and mixtures of various mono-, di- and tri-O-methylated derivatives are usually obtained.

Moreover, prior art investigations showed that (Bioorg.Med.Chem.Lett., 8 (1998)549) the relative reactivity of hydroxyl groups under the classical O-methylation reaction conditions proceeds in following order: for the 8a-azalides 4"-OH>12-OH>>11-OH, for 9a-azalides 11-OH≧12-OH>4"-OH. It is important to mention that under even the most vigorous reaction conditions O-methylation of 8a- and 9a-azalide 6-OH group does not occur. This is in contrast to the O-methylation of erythromycin in which system the 6-OH is easily methylated under conditions very similar to these (J.Antibiotics 43 (1990)286). However, in all cases mixtures of various mono-, and di- and tri-O-methylated derivatives are generally obtained. The relative rates of methylation of the hydroxyls presumably depend on subtle conformation details and are not predictable by a cursory inspection of the structure.

On the other hand substantially or partially regioselective, but not complete, regioselective methylation of various monosaccharides and nucleosides with diazomethane in the presence of transition-metal halides or boric acid has been described in the literature, [Carb.Res. 316 (1990) 187; Helv. Chim. Acta 79 (1996) 2114-2136; Chem.Pharm.Bull., 18 (1970) 677; Carb.Res., 91 (1981) 31], but it has not been possible to predict the site of methylation. Moreover, there are no known reports of regioselective O-alkylation of the 11-hydroxyl group of macrolides and azalides with diazoalkanes in the presence of transition-metal halides or boric acid In connection with these reported observations, the exclusive (complete) regioselective 11-O-methylation by the process of the present invention is unique and not obvious.

SUMMARY OF THE INVENTION

In one aspect, the present invention relates to a process for regioselective O-alkylation of macrolides and azalides, for the preparation of 11-O-alkyl compounds of formula (I) and pharmaceutically acceptable salts and solvates thereof.

(I)

wherein

A is derived from either a 14-membered macrolide or a 15-membered azalide, and $R^1$ is a C1-C4 alkyl group, which process comprises, reacting a macrolide or azalide having vicinal hydroxyls of formula (II)

(II)

with a diazoalkane of formula (III):

(III)

wherein $R^2$ is hydrogen or a C1-C3 alkyl group in the presence of a catalyst of a transition-metal halide or boric acid, preferably $H_3BO_3$, $TiCl_4$ or $SnCl_2$, in a suitable inert organic solvent.

Preferably, the 14- and 15-membered macrolides and azalides reacted in the process of the present invention have the formula (IV)

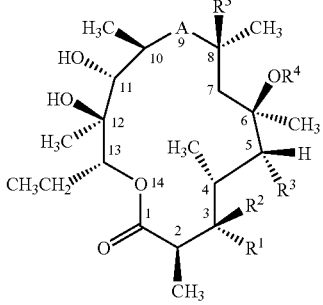
(IV)

wherein
A is a bivalent radical selected from —C(O)—, —C(O)NH—, —NHC(O)—, —N($R^{11}$)—CH$_2$—, —CH$_2$—N($R^{11}$)—, —CH(N$R^{11}R^{12}$)— and —C(=N—O$R^{13}$)—;
$R^1$ is cladinosyl of formula (V), OH or together with $R^2$ forms a keto group provided that when $R^1$ together with $R^2$ forms a keto group $R^4$ is not H;

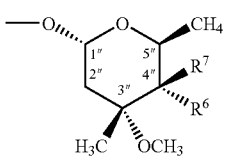
(V)

$R^2$ is H or together with $R^1$ forms a keto group;
$R^3$ is desosaminyl of formula (VI) or hydroxyl;

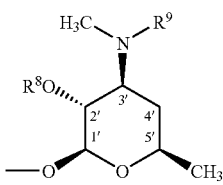
(VI)

$R^4$ is hydrogen, $C_{1-4}$alkyl, or $C_{2-6}$alkenyl optionally substituted by 9 to 10 membered fused bicyclic heteroaryl;
$R^5$ is hydrogen or fluorine;
$R^6$ is hydroxyl, —NH$_2$, or together with $R^7$ forms a keto group or =N$R^{10}$;
$R^7$ is hydrogen, —NH$_2$, or together with $R^6$ forms a keto group or =N$R^{10}$;
$R^8$ is H or a carbobenzoxy group;
$R^9$ is H, CH$_3$ or a carbobenzoxy group;
$R^{10}$ is hydrogen or $C_{1-6}$alkyl;
$R^{11}$ and $R^{12}$ are each independently hydrogen, $C_{1-6}$alkyl, aryl, heteroaryl, heterocyclyl, sulfoalkyl, sulfoaryl, sulfoheterocyclyl or —C(O)$R^{10}$, wherein the alkyl, aryl and heterocyclyl groups are optionally substituted by up to three groups independently selected from $R^{14}$;
$R^{13}$ is hydrogen, —$C_{1-6}$alkyl, $C_{2-6}$alkenyl, —(CH$_2$)$_a$aryl, —(CH$_2$)$_a$heterocyclyl, or —(CH$_2$)$_a$O(CH$_2$)$_b$O$R^{10}$;
$R^{14}$ is halogen, cyano, nitro, hydroxyl, $C_{1-6}$alkyl, C1-6alkoxy or aryloxy, C1-6alkythio or arythio, —NH$_2$, —NH(C$_{1-6}$alkyl), or —N(C$_{1-6}$alkyl)$_2$; and
a and b are each independently integers from 1 to 4

The process may be utilized to prepare 11-O-alkyl macrolides, including, but not limited to 11-O-alkyl derivatives of clarithromycin (J. Antibiot. 43 (1990) 544-549) and roxithromycin (J. Antibiot 39 (1986) 660). The process of the present invention, may also be used to prepare 11-O-alkyl azalides including, but not limited to 11-O-alkyl derivatives of azithromycin (J. Chem. Research (S) (1988) 152, J. Chem. Research (M) (1988) 1239), 2'-O,3'-N-dicarbobenzoxy-azithromycin (J. Antibiotics 45 (1992) 527), 9-deoxo-9a-aza-9a-homoerythromycin (J. Chem. Soc. Perkin Trans. 1 (1986) 1881), 3-decladinosyl-5-dedesosaminyl-9-deoxo-9a-aza-9a-homoerythromycin(J. Chem. Soc. Perkin Trans. 1 (1986) 1881-1890), 8a-aza-8a-homoerythromycin (Bioorg. Med. Chem. Lett. 3 (1993) 287).

In another aspect, the invention relates to 11-O-alkyl azalides of formula (VIIa):

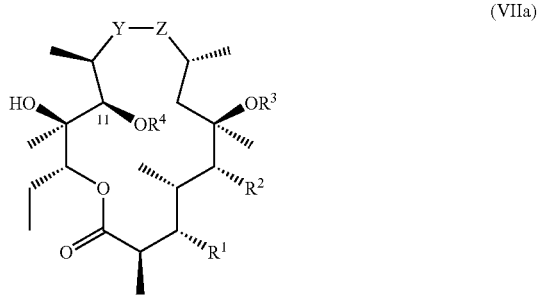
(VIIa)

wherein
Y is nitrogen and Z is the bivalent radical —CH$_2$—, or Y is —C(O)— and Z is nitrogen;
$R^1$ is OH or cladinosyl of formula (V);

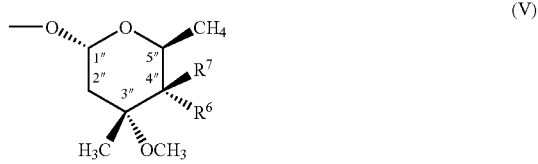
(V)

wherein
$R^6$ is hydroxyl;
$R^7$ is hydrogen;
$R^2$ is hydroxyl, or desosaminyl of formula (VIII):

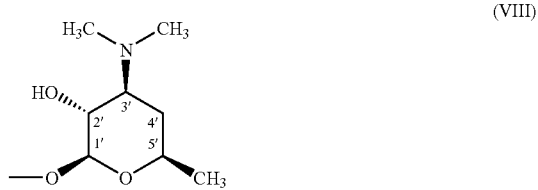
(VIII)

$R^3$ is hydrogen or a CH$_3$ group; and
$R^4$ is a $C_1$-$C_4$ alkyl group;
or an 11-O-alkyl macrolide of formula (VIIb)

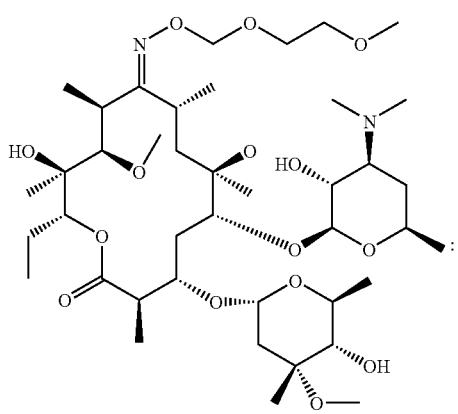

(VIIb)

and pharmaceutically acceptable salts and solvates thereof and uses thereof as antibacterial agents or intermediates for the synthesis of other antibacterial agents.

DETAILED DESCRIPTION OF THE INVENTION

As used herein, the following terms are defined as follows:

The term "regioselective" refers to a reaction in which one direction of bond formation or elimination occurs preferentially over all other possible alternatives; reactions are termed completely (100%) regioselective if the selectivity is complete, or substantially regioselective (at least about 75 molar %), or partially (at least about 50 molar %), if the product of reaction at the specified site predominates over the products of reaction at other sites.

The term "alkyl" as used herein as a group or a part of a group refers to a straight or branched hydrocarbon chain containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, isopropyl, t-butyl and hexyl.

The term "alkenyl" as used herein as a group or a part of a group refers to a straight or branched hydrocarbon chain containing the specified number of carbon atoms and containing at least one double bond. For example, the term "$C_{2-6}$alkenyl" means a straight or branched alkenyl containing at least 2, and at most 6, carbon atoms and containing at least one double bond. Examples of "alkenyl" as used herein include, but are not limited to, ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl.

The term "alkoxy" as used herein refers to a straight or branched chain alkoxy group containing the specified number of carbon atoms. For example, $C_{1-6}$alkoxy means a straight or branched alkoxy containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. A $C_{1-4}$alkoxy group is preferred, for example methoxy, ethoxy, propoxy, prop-2-oxy, butoxy, but-2-oxy or 2-methylprop-2-oxy.

The term "aryl" as used herein refers to an aromatic carbocyclic moiety such as phenyl, biphenyl or naphthyl.

The term "heteroaryl" as used herein, unless otherwise defined, refers to an aromatic heterocycle of 5 to 10 members, having at least one hetero atom selected from nitrogen, oxygen and sulfur, and containing at least 1 carbon atom, including both mono and bicyclic ring systems. Examples of heteroaryl rings include, but are not limited to, furanyl, thiophenyl, pyrrolyl, pyrazolyl, imidazolyl, oxazolyl, isoxazolyl, thiazolyl, isothiazolyl, triazolyl, oxadiazolyl, tetrazolyl, thiadiazolyl, pyridyl, pyridazinyl, pyrazinyl, pyrimidinyl, triazinyl, quinolinyl, isoquinolinyl, 1,2,3,4-tetrahydroisoquinolinyl, benzofuranyl, benzimidazolyl, benzothienyl, benzoxazolyl, 1,3-benzodioxazolyl, indolyl, benzothiazolyl, furylpyridine, oxazolopyridyl and benzothiophenyl.

The term "9 to 10 membered fused bicyclic heteroaryl" as used herein as a group or a part of a group refers to quinolinyl, isoquinolinyl, 1,2,3,4-tetrahydroisoquinolinyl, benzofuranyl, benzimidazolyl, benzothienyl, benzoxazolyl, 1,3-benzodioxazolyl, indolyl, benzothiazolyl, furylpyridine, oxazolopyridyl or benzothiophenyl.

The term "heterocyclyl" as used herein, unless otherwise defined, refers to a monocyclic or bicyclic three- to ten-membered saturated or non-aromatic, unsaturated hydrocarbon ring containing at least one heteroatom selected from oxygen, nitrogen and sulfur. Preferably, the heterocyclyl ring has five or six ring atoms. Examples of heterocyclyl groups include, but are not limited to, pyrrolidinyl, tetrahydrofuranyl, tetrahydrothiophenyl, imidazolidinyl, pyrazolidinyl, piperidyl, piperazinyl, morpholino, tetrahydropyranyl and thiomorpholino.

The term "halogen" refers to a fluorine, chlorine, bromine or iodine atom.

The term "lower alcohol" refers to alcohols having between one and six carbons, including, but not limited to, methanol, ethanol, propanol, and isopropanol.

The term "aprotic solvent" refers to a solvent that is relatively inert to proton activity, i.e. not acting as a proton donor; examples include, but are not limited to, hydrocarbons such as hexane and toluene; halogenated hydrocarbons such as methylene chloride, ethylene chloride and chloroform; ethers such as diethylether and diisopropylether; acetonitrile; amines such as N,N-dimethylformamide, N,N-dimethylacetamide, and pyridine; and lower aliphatic ketones, such as acetone and dimethyl sulfoxide.

The term "protic solvent" refers to a solvent that displays a high degree of proton activity, i.e., is a proton donor; examples of protic solvents include, but are not limited to, lower alcohols, such as methanol, ethanol, propanol, and isopropanol.

Suitable "pharmaceutically acceptable salts" are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, isonicotinate, salicylate, pantothenate, maleate, malate, fumarate, lactate, tartrate, bitartrate, ascorbate, citrate, formate, gluconate, succinate, pyruvate, oxalate, oxaloacetate, trifluoroacetate, saccharate, benzoate, alkyl or aryl sulphonates (e.g., methanesulphonate, ethanesulphonate, benzenesulphonate or p-toluenesulphonate), pamoate (i.e., 1,1'-methylene-bis-(2-hydroxy-3naphthoate)) and isethionate.

Typically, a pharmaceutically acceptable salt may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula (I) and the resulting mixture evaporated to dryness (lyophilized) to obtain the acid addition salt as a solid. Alternatively, a compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Those skilled in the art of organic chemistry will appreciate that many organic compounds and their salts can form complexes with solvents in which they are reacted or from which they are precipitated or crystallized. These complexes are known as "solvates". For example, a complex with water is known as a "hydrate" and a complex with ethanol is known as an "ethanolate". Solvates of the compounds of this invention or salts thereof are within the scope of the invention.

In one aspect of the present invention, macrolide and azalide derivatives of formula (II) are dissolved in an inert organic solvent. Suitable solvents include, but are not limited to, protic and aprotic solvents, preferably, lower alcohols, acetonitrile, acetone, N,N-dimethylformamide, N,N-dimethylacetamide, pyridine, dichloromethane, ethyl-acetate, dimethyl sulfoxide, or ethers, and most desirably acetone, ethanol, acetonitrile or N,N-dimethylformamide.

To the dissolved macrolide or azalide the catalyst is added in a molar ratio of from about 1:0.05 to about 1:4, preferably from 1:0.25 to about 1:2.

Preferably, the catalyst is boric acid or a transition-metal halide, most desirably boric acid or $TiCl_4$ or $SnCl_2$. To the reaction mixture a diazoalkane prepared according to the methods described in J. Org. Chem. 45 (1980) 5377-5378 or Org. Synth. Coll. Vol. 2 (1943) 165 is added. The resulting mixture is stirred at a temperature from about −20° C. to about the reflux temperature of the solvent, preferably from about 0° C. to about 40° C., and most desirably from about 15° C. to about 30° C. The mixture is stirred for a period from about 30 minutes to about 8 hours, preferably from about 1 hour to about 6 hours.

Isolation using standard methods (extraction, precipitation or the like) affords the desired 11-O-alkyl macrolide or azalide derivative in completely (100%) regioselective purity.

Compounds according to the invention exhibit a broad spectrum of antimicrobial activity, in particular antibacterial activity, against a wide range of clinical pathogenic microorganisms. Using a standard microtiter broth serial dilution test, compounds of the invention have been found to exhibit useful levels of activity against a wide range of pathogenic microorganisims. In particular, the compounds of the invention may be active against strains of *Staphylococcus aureus, Streptococcus pneumoniae, Moraxella catarrhalis, Streptococcus pyogenes,* or *Haemophilus influenzae*. The compounds of the present invention exhibit better activity against inducible (*S. pyogenes* B0543) and efflux (*S. pyogenes* B0545) resistant strains than the parent compounds. (Table 1.)

TABLE 1

MIC's of Selected Compounds

| Microorganism | 9-Deoxo-9a-aza-9a-homoerythromycin | Ex. 3 | 8a-Aza-8a-homo-erythromycin | Ex. 5 |
| --- | --- | --- | --- | --- |
| S. aureus B0329 | 4 | 1 | 2 | 0.5 |
| S. pneumoniae B0541 | 0.25 | 0.125 | 0.125 | 0.125 |

TABLE 1-continued

MIC's of Selected Compounds

| Microorganism | 9-Deoxo-9a-aza-9a-homoerythromycin | Ex. 3 | 8a-Aza-8a-homo-erythromycin | Ex. 5 |
| --- | --- | --- | --- | --- |
| S. pneumoniae B0326 M | 16 | 8 | 64 | 32 |
| S. pyogenes B0542 | 0.125 | 0.125 | 0.25 | 0.125 |
| S. pyogenes B0543 iMLS | 32 | 16 | 8 | 4 |
| S. pyogenes B0545 M | 16 | 4 | 32 | 16 |
| M. catarrhalis B0324 | 1 | 0.125 | 2 | 0.125 |
| H. influenzae B0529 | 0.5 | 0.5 | 1 | 1 |
| E. coli B0001 | 4 | 2 | 16 | 16 |

The compounds of formula (VIIa) and (VIIb) may be administred orally or parenterally in conventional dosage forms such as tablet, capsule, powder, troches, dry mixes, ointment, suspension or solution prepared according to conventional pharmaceutical practices.

The compounds of formula (VIIa) and (VIIb) can be administred at a dosage of from about 1 mg/kg to about 1000 mg/kg of body weight per day. The preferred dosage range is from about 5 mg/kg to about 200 mg/kg of body weight per day.

The process of this invention will be best understood in connection with the following examples, which are intended as an illustration of and not a limitation upon the scope of the invention as defined in the appended claims.

Experimental:

Starting compounds were prepared according to published methods the disclosures of which are herein incorporated by reference.

Preparation of Diazomethane

Method A

Diazomethane was prepared according to the method and apparatus described in J. Org. Chem. 45 (1980) 5377-5378, starting from N-methyl-N-nitroso-p-toluensulfonamide (Diazald) and potassium hydroxide. A solution of Diazald in diethylether was added dropwise to a solution of KOH in water and ethanol. The yellow condensate of diazomethane was continuously introduced into the reaction mixture.

Method B

Diazomethane was prepared according to the method described in Org. Synth. Coll. Vol. 2 (1943) 165, starting from N-methyl-N-nitrosourea which was added portionwise to the mixture of 40% aq. KOH and diethyl or diisopropyl-ether at 0° C. with vigorous stirring. The phases were separated and the upper organic layer containing diazomethane was used for methylation.

EXAMPLE 1

11-O-METHYL-AZITHROMYCIN

Method I

Azithromycin (75 g, 0.1 mol) and boric acid (3.1 g, 0.05 mol) were dissolved in absolute ethanol (300 mL) and the yellow condensate of diazomethane (cca 0.27 mol) obtained in method A was continuously added to the the reaction mixture dropwise. The mixture was stirred at room temperature for 6 hours. A few drops of acetic acid were added to remove diazomethane excess. Ether was removed under reduced pressure followed by evaporation of ethanol to a volume of 200 mL. The product was percipitated by adding 400 mL of water. The crude product was dried in a vacuum oven for 12 hours at 40° C. Yield was 87%. The product was crystallized from ethanol/water to afford 100% pure (LC-MS analysis) 11-O-methyl-azithromycin in 73% yield.

ES-MS: m/z 763.2 (M+H), 605.3 (M+H-cladinose)

$^1$H NMR(500 MHz, CDCl$_3$): δ(ppm) 3.59 (s, 3H, 11-OMe), 3.42 (d, 1H, 11-H), 3.25 (dd, 1H, 2'-H), 3.03 (t, 1H, 4"-H)

$^{13}$C NMR(125 MHz, CDCl$_3$): δ(ppm) 85.0 (11-C), 78.2 (4"-C), 70.9 (2'-C) 62.1 (11-OMe)

Method II

Azithromycin (1.012 g, 1.35 mmol) and boric acid (0.0885 g, 1.43 mmol) were dissolved in acetonitrile (20 mL) and stirred at RT for 1 hour. A solution of diazomethane in diethylether prepared by Method B (cca 6 mmol) was added and the resulting mixture was stirred at RT for 2 hours. The mixture was diluted with aq. NaHCO$_3$ (50 mL) and extracted with ethyl-acetate (3×30 mL). The organic layer was dried over Na$_2$SO$_4$, and concentrated to afford the title compound (0.702 g, yield 68%).

The compound of Example 1 was obtained in the same manner as described in Example 1, Method II, with the use of different solvents and catalysts as indicated in Table 2. Quantitative analysis of the final mixtures was performed by the LC-MS method.

TABLE 2

Preparation of 11-O-methyl azithromycin, according to Example 1.

| Solvent | Catalyst | Azithromycin | Yield of 11-OMe-azithromycin | By-product |
|---------|----------|--------------|------------------------------|------------|
| DMF | SnCl$_2$ | 33% | 47% | 20% |
| DMF | H$_3$BO$_3$ | — | 99% | 1% |
| MeCN | H$_3$BO$_3$ | — | 99% | 1% |
| MeOH | H$_3$BO$_3$ | — | 73% | 23% |
| acetone | H$_3$BO$_3$ | 2.5% | 95% | 2.5% |
| diglyme | H$_3$BO$_3$ | 36.3% | 61.6% | 1.2% |
| EtOH | H$_3$BO$_3$ | — | 72.7% | 26.5% |
| i-PrOH | H$_3$BO$_3$ | 39.3% | 43% | 17.5% |

EXAMPLE 2

11-O-METHYL-2'-O,3'-N-DICARBOBENZOXY-AZITHROMYCIN

2'-O,3'-N-Dicarbobenzoxy-azithromycin (J. Antibiotics 45 (1992) 527-534) (0.204 g, 0.203 mmol) and TiCl$_4$ (0.040 g, 0.210. mmol) were dissolved in DMF (5 mL) and stirred at RT for 1 hour. A solution of diazomethane in diethylether from Method B (cca 4 mmol) was added and the resulting mixture was stirred at RT for 6 hours. The mixture was diluted with aq. NaHCO$_3$ (50 mL) and extracted with ethyl-acetate (3×30 mL). The organic layer was dried over Na$_2$SO$_4$, and concentrated to afford the title compound.

ES-MS: m/z 1017.3 (M+H), 859.4 (M+H-cladinose)

EXAMPLE 3

11-O-METHYL-9-DEOZO-9A-AZA-9A-HOMOERYTHROMYCIN

9-Deoxo-9a-aza-9a-homoerythromycin (J. Chem. Soc. Perkin Trans. 1 (1986) 1881-1890) (1.00 g, 1.36 mmol) and H$_3$BO$_3$ (0.084 g, 1.36 mmol) were dissolved in acetonitrile (20 mL) and stirred at RT for 1 hour. A solution of diazomethane in diethylether prepared by Method B (cca 6 mmol) was added and the resulting mixture was stirred at RT for 2 hours. The mixture was diluted with aq. NaHCO$_3$ (50 mL) and extracted with ethyl-acetate (3×30 mL). The organic layer was dried over Na$_2$SO$_4$, and concentrated to afford the title compound (0.813 g, yield 80%).

ES-MS: m/z 749.6 (M+H), 591.5 (M+H-cladinose)

$^1$H NMR(500 MHz, CDCl$_3$): δ(ppm) 3.56 (s, 3H, 11-OMe), 3.43 (d, 1H, 11-H), 3.30 (dd, 1H, 2'-H), 3.03 (t, 1H, 4"-H)

$^{13}$C NMR(125 MHz, CDCl$_3$): δ(ppm) 84.3 (11-C), 78.1 (4"-C), 70.9 (2'-C) 62.4 (11-OMe)

EXAMPLE 4

11-O-METHYL-3-DECLADINOSYL-5-DEDESOSAMINYL-9-DEOXO-9A-AZA-9A-HOMO-ERYTHROMYCIN

3-Decladinosyl-5-dedesosaminyl-9-deoxo-9a-aza-9a-homoerythromycin (J. Chem. Soc. Perkin Trans. 1 (1986) 1881-1890) (0.201 g, 0.48 mmol) and H$_3$BO$_3$ (0.040 g, 0.64 mmol) were dissolved in ethanol (20 mL) and stirred at RT for 1 hour. A solution of diazomethane in diethylether prepared by Method B (cca 3 mmol) was added and the resulting mixture was stirred at RT for 4 hours. The mixture was diluted with aq. NaHCO$_3$ (20 mL) and extracted with ethyl-acetate (3×20 mL). The organic layer was dried over Na$_2$SO$_4$, and concentrated to afford the title compound (0.106 g, yield 51%).

ES-MS: m/z 434.3 (M+H)

$^1$H NMR(500 MHz, DMSO): δ(ppm) 4.64 (d, 1H, 3-OH), 3.68 (d, 1H, 5-OH), 3.48 (s, 3H, 11-OMe), 3.42 (t, 1H, 3-H), 3.31 (1H, 5-H), 3.18 (d, 1H, 6-OH), 3.14 (d, 1H, 11-H)

$^{13}$C NMR(125 MHz, DMSO): δ(ppm) 85.6 (11-C), 83.1 (5-C), 79.7 (3-C), 73.3 (6-C) 61.4 (11-OMe)

EXAMPLE 5

11-O-METHYL-8A-AZA-8A-HOMOERYTHROMYCIN

8a-Aza-8a-homoerythromycin (Bioorg. Med. Chem. Lett. 3 (1993) 1287) (1.00 g, 1.34 mmol) and H$_3$BO$_3$ (0.084 g, 1.36 mmol) were dissolved in acetone (10 mL) and stirred at RT for 1 hour. A solution of diazomethane in diethylether prepared by Method B (cca 6 mmol) was added and the resulting mixture was stirred at RT for 4 hours. The mixture was diluted with aq. NaHCO$_3$ (50 mL) and extracted with ethyl-acetate (3×30 mL). The organic layer was dried over Na$_2$SO$_4$, and concentrated to afford the title compound (0.740 g, yield 71%).

ES-MS: m/z 763.3 (M+H), 605.3 (M+H-cladinose)
$^1$H NMR(500 MHz, CDCl$_3$): δ(ppm) 3.48 (s, 3H, 11-OMe), 3.27 (dd, 1H, 2'-H), 3.17 (d, 1H, 11-H), 3.06 (t, 1H, 4''-H)
$^{13}$C NMR(125 MHz, CDCl$_3$): δ(ppm) 79.5 (11-C), 77.5 (4''-C), 70.0 (2'-C) 59.9 (11-OMe)

EXAMPLE 6

11-O-METHYL-ROXITHROMYCIN

Roxithromycin (J. Antibiot 39 (1986) 660) (1.00 g, 1.20 mmol) and H$_3$BO$_3$ (0.042 g, 0.68 mmol) were dissolved in acetone (10 mL) and stirred at RT for 1 hour. A solution of diazomethane in diethylether prepared by Method B (cca 6 mmol) was added and the resulting mixture was stirred at RT for 4 hours. The mixture was diluted with aq. NaHCO$_3$ (50 mL) and extracted with ethyl-acetate (3×30 mL). The organic layer was dried over Na$_2$SO$_4$, and concentrated to afford a mixture of the title and starting compounds (70%:30% LC-MS).

ES-MS: m/z 851.3 (M+H)
$^1$H NMR(500 MHz, CDCl$_3$): δ(ppm) 3.63 (s, 3H, 11-OMe), 3.53 (d, 1H, 11-H), 3.33 (1H, 2'-H), 3.03 (1H, 4''-H)
$^{13}$C NMR(125 MHz, CDCl$_3$): δ(ppm) 79.8 (11-C), 77.9 (4''-C), 70.9 (2'-C) 62.1 (11-OMe)

EXAMPLE 7

11-O-METHYL-CLARITHROMYCIN

Clarithromycin (J. Antibiot. 43 (1990) 544-549) (1.00 g, 1.34 mmol) and SnCl$_2$ 2H$_2$O (0.307 g, 1.36 mmol) were dissolved in DMF (10 mL) and stirred at RT for 1 hour. A solution of diazomethane in diethylether prepared by Method B (cca 6 mmol) was added and the resulting mixture was stirred at RT for 4 hours. The mixture was diluted with aq. NaHCO$_3$ (50 mL) and extracted with ethyl-acetate (3×30 mL). The organic layer was dried over Na$_2$SO$_4$, and concentrated to afford a mixture of the title and starting compounds (24%:73% LC-MS).

ES-MS: m/z 762.4 (M+H) 604.3 (M+H-cladinose)

EXAMPLE 8

11-O-METHYL-3-DECLADINOSYL-5-DESOSAMINYL-9-DEOXO-9A-AZA-9A-HOMOERYTHROMYCIN A

Starting from 3-decladinosyl-5-desosaminyl-9-deoxo-9a-aza-9a-homoerythromycin A (J. Chem. Soc. Perkin Trans. 1 (1986) 1881-1890) the title compound is prepared according to the procedure described in Example 4.

EXAMPLE 9

11-O-METHYL-3-DECLADINOSYL-5-DESOSAMINYL-8A-AZA-8A-HOMOERYTHROMYCIN A a) Starting from 8a-aza-8a-homoerythromycin A (Bioorg. Med. Chem. Lett 3 (1993) 1287) the 3-decladinosyl-5-desosaminyl-8a-aza-8a-homoerythromycin is prepared according to the procedure described in Example 4 of International Patent Application WO99/51616.

b) Starting from the compound prepared in Step a) the title compound is prepared according to the procedure described in Example 4.

EXAMPLE 10

11-O-METHYL-3-DECLADINOSYL-5-DEDESOSAMINYL-8A-AZA-8A-HOMOERYTHROMYCIN A a) Starting from the compound prepared in Example 9, Step a) the desosamine is cleaved according to the procedure published in J. Chem. Soc. Perkin Trans. 1 (1986) 1881-1890 for compound 13.
b) Starting from the compound prepared in Step a) the title compound is prepared according to the procedure described in Example 4.

EXAMPLE 11

6,11-DI-O-METHYL-8A-AZA-8A-HOMOERYTHROMYCIN A

Starting from 6-O-Methyl-8a-aza-8a-homoerthromycin A (WO99/51616, Example 3) the title compound is prepared according to the procedure described in Example 4.

EXAMPLE 12

6,11-DI-O-METHYL-3-DECLADINOSYL-5-DESOSAMINYL-8A-AZA-8A-HOMOERYTHROMYCIN A

Starting from 3-decladinosyl-6-O-Methyl-8a-aza-8a-homoerthromycin A (WO99/51616, Example 5) the title compound is prepared according to the procedure described in Example 4.

EXAMPLE 13

6,11-DI-O-METHYL-3-DECLADINOSYL-5-DEDESOSAMINYL-8A-AZA-8A-HOMOERYTHROMYCIN A a) Starting from 3-decladinosyl-6-O-Methyl-8a-aza-8a-homoerthromycin A (WO99/51616, Example 5) the desosamine is cleaved according to the procedure published in J. Chem. Soc. Perkin Trans. 1 (1986) 1881-1890 for compound 13.
b) Starting from the compound prepared in Step a) the title compound is prepared according to the procedure described in Example 4.

EXAMPLE 14

HYDROCHLORIDE SALT OF 11-O-METHYL-AZITHROMYCIN

11-O-Methyl-azithromycin of Example 1 (1.0 g, 1.31 mmol) was dissolved in i-PrOH (20 ml) and a few drops of dichloromethane and then HCl (5M solution in i-PrOH, 2.05 eqv) was added. The hydrochloride salt was isolated by precipitation with (i-Pr)$_2$O giving 0.85 g of the title compound.

What is claimed is:
1. A process for the preparation of a compound of the formula

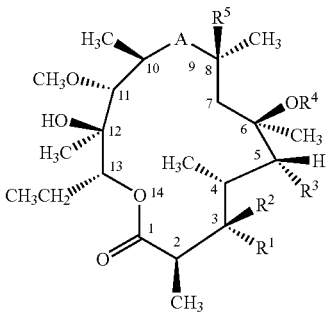

wherein:

A is a bivalent radical selected from —C(O)—, —C(O)NH—, —NHC(O)—, —N($R^{11}$)—$CH_2$—, —$CH_2$—N($R^{11}$)—, —CH(N$R^{11}R^{12}$)— and —C(=N—O$R^{13}$)—;

$R^1$ is cladinosyl of formula (V), OH or together with $R^2$ forms a keto group provided that when $R^1$ together with $R^2$ forms a keto group $R^4$ is not H;

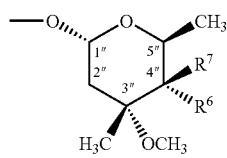

(V)

$R^2$ is H or together with $R^1$ forms a keto group;
$R^3$ is desosaminyl of formula (VI) or hydroxyl;

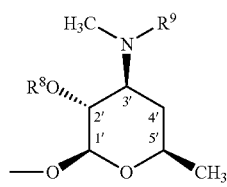

(VI)

$R^4$ is hydrogen, $C_{1-4}$alkyl, or $C_{2-6}$alkenyl optionally substituted by 9 to 10 membered fused bicyclic heteroaryl;
$R^5$ is hydrogen or fluorine;
$R^6$ is hydroxyl, —$NH_2$, or together with $R^7$ forms a keto group or =N$R^{10}$;
$R^7$ is hydrogen, —$NH_2$, or together with $R^6$ forms a keto group or =N$R^{10}$;
$R^8$ is H or a carbobenzoxy group;
$R^9$ is H, $CH_3$ or a carbobenzoxy group;

$R^{10}$ is hydrogen or $C_{1-6}$alkyl;
$R^{11}$ and $R^{12}$ are each independently hydrogen, $C_{1-6}$alkyl, aryl, heteroaryl, heterocyclyl, sulfoalkyl, sulfoaryl, sulfoheterocyclyl or —C(O)$R^{10}$, wherein the alkyl, aryl and heterocyclyl groups are optionally substituted by up to three groups independently selected from $R^{14}$;
$R^{13}$ is hydrogen, —$C_{1-6}$alkyl, $C_{2-6}$alkenyl, —$(CH_2)_a$aryl, —$(CH_2)_a$heterocyclyl, or —$(CH_2)_aO(CH_2)_bOR^{10}$;
$R^{14}$ is halogen, cyano, nitro, hydroxyl, $C_{1-6}$alkyl, C1-6alkoxy or aryloxy, C1-6alkythio or arylthio, —$NH_2$, —NH($C_{1-6}$alkyl) or —N($C_{1-6}$alkyl)$_2$; and
a and b are each independently integers from 1 to 4;
comprising the step of O-methylating at the 11 position a compound of formula (IV)

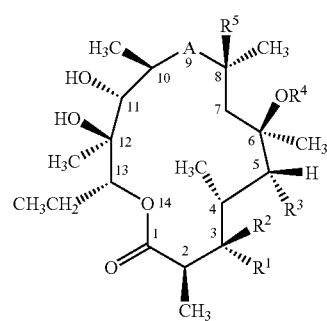

(IV)

wherein A and $R^1$-$R^{14}$ are as hereinbefore defined, with a diazomethane of formula (III)

$R^2$—CH $N_2$ (III)

wherein:
$R^2$ is hydrogen,
in the presence of a catalyst selected from the group consisting of $TiCl_4$, $SnCl_2$ and boric acid, and in an inert organic solvent selected from the group consisting of acetone, ethanol, acetonitrile and N,N-dimethylformamide, wherein the molar ratio of a compound of formula (IV) to catalyst is 1: 0.25 to 1: 2, and wherein said methylating step results in substantial regioselectivity.

2. The process according to claim 1, wherein a compound of formula (IV) is selected from the group consisting of azithromycin, 2'—O,3'—N-dicarbobenzoxy-azithromycin, 9-deoxo-9a-aza-9a-homoerythromycin, 3-decladinosyl-5-dedesosaminyl-9-deoxo-9a-aza-9a-homoerythromycin, 8a-aza-8a-homoerythromycin, roxithromycin, clarithromycin, 3-decladinosyl-5-desosaminyl-9-deoxo-9a-aza-9a-homoerythromycin, 3-decladinosyl-5-desosaminyl-8a-aza-8a-homoerythromycin and 3-decladinosyl-5-dedesosaminyl-8a-aza-8a-homoerythromycin.

* * * * *

UNITED STATES PATENT AND TRADEMARK OFFICE
CERTIFICATE OF CORRECTION

PATENT NO.       : 7,435,805 B2  
APPLICATION NO.  : 10/851768  
DATED            : October 14, 2008  
INVENTOR(S)      : Davor Kidemet et al.

It is certified that error appears in the above-identified patent and that said Letters Patent is hereby corrected as shown below:

ON THE TITLE PAGE:

At Item (73), Assignee, "GlaxpSmithkline" should read -- GlaxoSmithKline --

Signed and Sealed this

Twenty-fourth Day of February, 2009

JOHN DOLL  
*Acting Director of the United States Patent and Trademark Office*